United States Patent [19]

Sterzer et al.

[11] 4,311,154

[45] Jan. 19, 1982

[54] NONSYMMETRICAL BULB APPLICATOR FOR HYPERTHERMIC TREATMENT OF THE BODY

[75] Inventors: Fred Sterzer, Princeton; Robert W. Paglione, Robbinsville, both of N.J.

[73] Assignee: RCA Corporation, New York, N.Y.

[21] Appl. No.: 23,393

[22] Filed: Mar. 23, 1979

[51] Int. Cl.³ .............................................. A61N 1/40
[52] U.S. Cl. .................................... 128/804; 128/736
[58] Field of Search ..................... 128/804, 788, 736; 219/10, 55 B

[56] References Cited

U.S. PATENT DOCUMENTS

| | | | |
|---|---|---|---|
| 2,126,257 | 8/1938 | Hird | 128/804 |
| 2,407,690 | 9/1946 | Southworth | 128/804 |
| 3,527,227 | 9/1970 | Fritz | 128/804 |
| 4,154,246 | 5/1979 | Le Veen | 128/804 |
| 4,204,549 | 5/1980 | Paglione | 128/804 X |

FOREIGN PATENT DOCUMENTS

| | | | |
|---|---|---|---|
| 1143937 | 7/1960 | Fed. Rep. of Germany | 128/804 |
| 431672 | 7/1935 | United Kingdom | 128/804 |
| 458534 | 12/1936 | United Kingdom | 128/804 |
| 762734 | 12/1956 | United Kingdom | 128/804 |
| 862646 | 3/1961 | United Kingdom | 128/804 |
| 1188110 | 4/1970 | United Kingdom | 128/804 |

OTHER PUBLICATIONS

Ely, T. S. et al., "Heating Characteristics of Lab Animals Exposed to Ten-Centimeter Waves", IEEE Trans-BME, Oct. '64, pp. 123-137.

Primary Examiner—Robert W. Michell
Assistant Examiner—Francis J. Jaworski
Attorney, Agent, or Firm—Samuel Cohen; Robert L. Troike; Christopher L. Maginniss

[57] ABSTRACT

Apparatus using microwave energy for the therapeutic and hyperthermic treatment of an internal body organ such as the prostate gland. An irregularly shaped coaxial applicator having a narrow portion and a wide portion is inserted through the male anus into the rectum such that a substantially maximum intensity of the microwave energy irradiates the prostrate gland for preferential heating of the prostate gland and a substantially minimum intensity irradiates untreated tissue. Temperature sensing means are positioned on the periphery of the applicator to measure the tissue environment irradiated by the microwave energy. A controller, operating with the temperature sensing means, is provided to maintain the temperature of the tissue environment within a desired temperature range.

7 Claims, 12 Drawing Figures

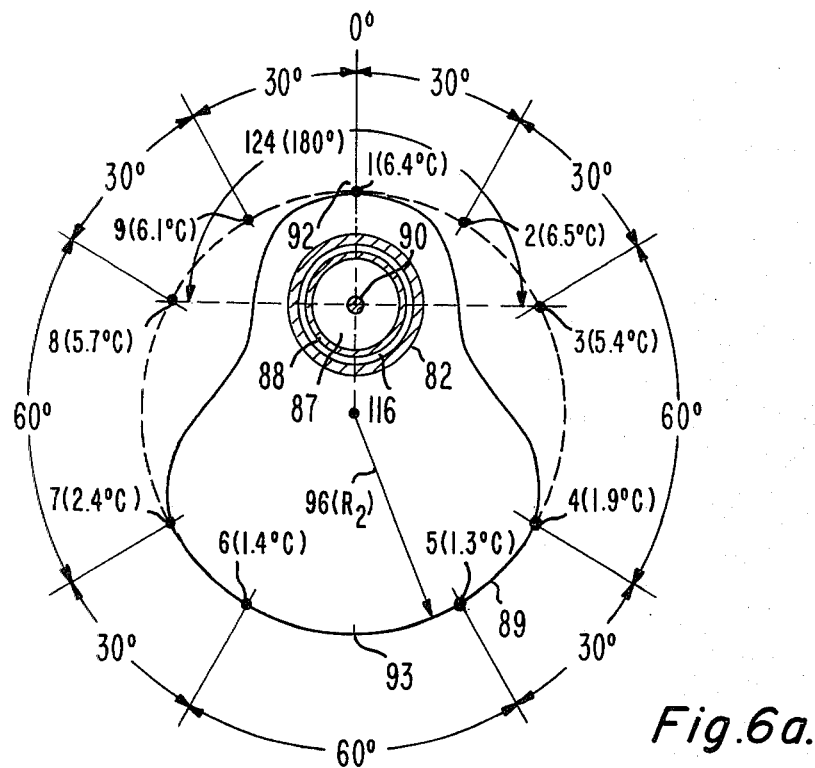
Fig.6a.
Fig.6b.
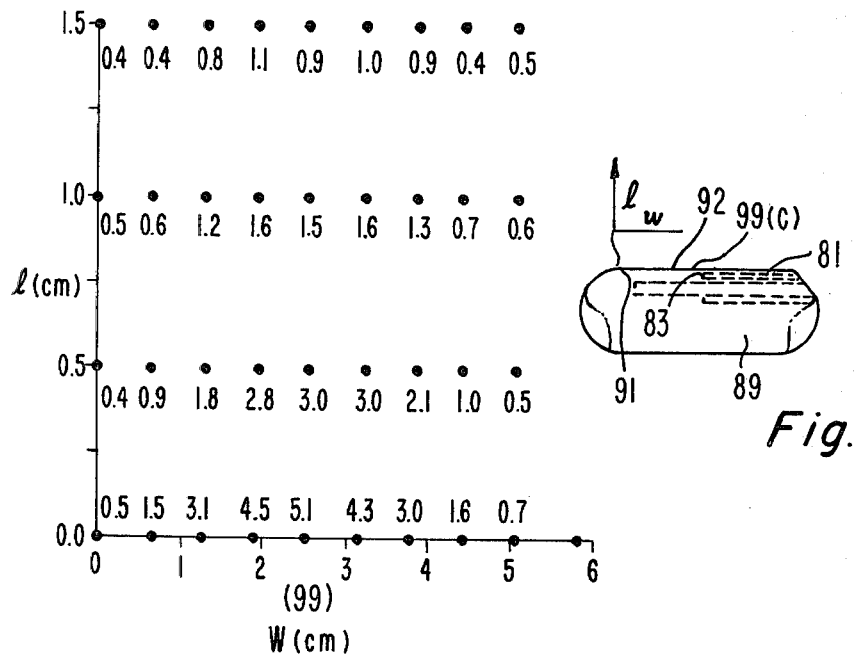
Fig.6c.

NONSYMMETRICAL BULB APPLICATOR FOR HYPERTHERMIC TREATMENT OF THE BODY

CROSS REFERENCE TO RELATED PATENTS

Of interest are the following patents: U.S. Pat. No. 4,204,549, entitled, "A Coaxial Applicator for Microwave Hyperthermia," issued to R. Paglione on May 27, 1980, and U.S. Pat. No. 4,190,053, entitled, "Apparatus for Hyperthermia Treatment," issued to F. Sterzer on Feb. 26, 1980. Both of these patents are assigned to the same assignee as the assignee of the present application.

BACKGROUND OF THE INVENTION

This invention relates to the use of microwave energy for the therapeutic treatment of a gland of the body and more particularly to an irregularly shaped microwave applicator positioned in the male rectum for the hyperthermia treatment of the prostate gland.

Medical practioners know that a patient with a cancerous tumor can be treated by a process which raises and maintains the temperature of the tumor to a predetermined value of about 43° C. This treatment is generally referred to as hyperthermia. One method of hyperthermia utilizes microwave energy. The temperature of the tissue irradiated by the microwave energy is a function of the powder or intensity of the microwave signal applied to the body tissue. The depth of penetration of the microwave signal into the tissue is generally a direct function of the type of tissue and an inverse function of the frequency of the signal applied. The dimensions of the shape of the irradiated volume of tissue are dependent on the parameters, such as, the type of tissue, the frequency of the microwave signal, and the radiation pattern of the microwave signal.

The microwave irradiation may be controlled to elevate the temperature of a volume of tissue. It is desirable to elevate the temperature of the treated tissue to the hyperthermic range while maintaining the temperature of an untreated tissue, within the general environment of the treated tissue, approximately at the normal body temperature. Various systems that apply microwave energy to the surface of the body for the hyperthermia treatment of subcutaneous tissue are known. One such system is described in the aforementioned U.S. Pat. No. 4,190,053. Microwave coaxial applicators having relatively small dimensions may be used for positioning within the body for hyperthermia treatment of subcutaneous tissue. Such a coaxial applicator is described in aforementioned U.S. Pat. No. 4,204,549. If the subcutaneous tissue to be treated is of a substantial volume and internally located in the lower abdomen of a body, the use of microwave energy applied to the surface of the body or the use of a coaxial applicator having relatively small dimensions may not provide sufficient microwave energy to heat and thereby raise the temperature of the prostate gland to the hyperthermia range.

It is now recognized that the use of microwave hyperthermia and radiotherapy procedures may be advantageous used in combination with each other.

An apparatus is provided using microwave energy for the therapeutic and hyperthermic treatment of an internal body organ such as the male prostate gland. A microwave source supplies a microwave signal having a predetermined amplitude and frequency. An applicator is provided that applies the microwave signal within an internal body cavity, such as a rectum, such that the rectal wall in close proximity to the prostate gland receives preferential heating relative to the rectal wall positioned diametrically opposite the prostate gland. Temperature sensing means positioned on the periphery of the applicator provides an electrical signal indicative of the temperature of the wall of the rectum in close proximity to the prostate gland. Control means, responsive to the temperature signal, couple the microwave signal to the applicator when the temperature of the rectal wall in close proximity to the prostate gland is less than a predetermined temperature.

IN THE DRAWING:

FIGS. 6A and 6B show heating patterns developed by the applicator (FIG. 6C) implanted in the ground beef.

Figure 1:
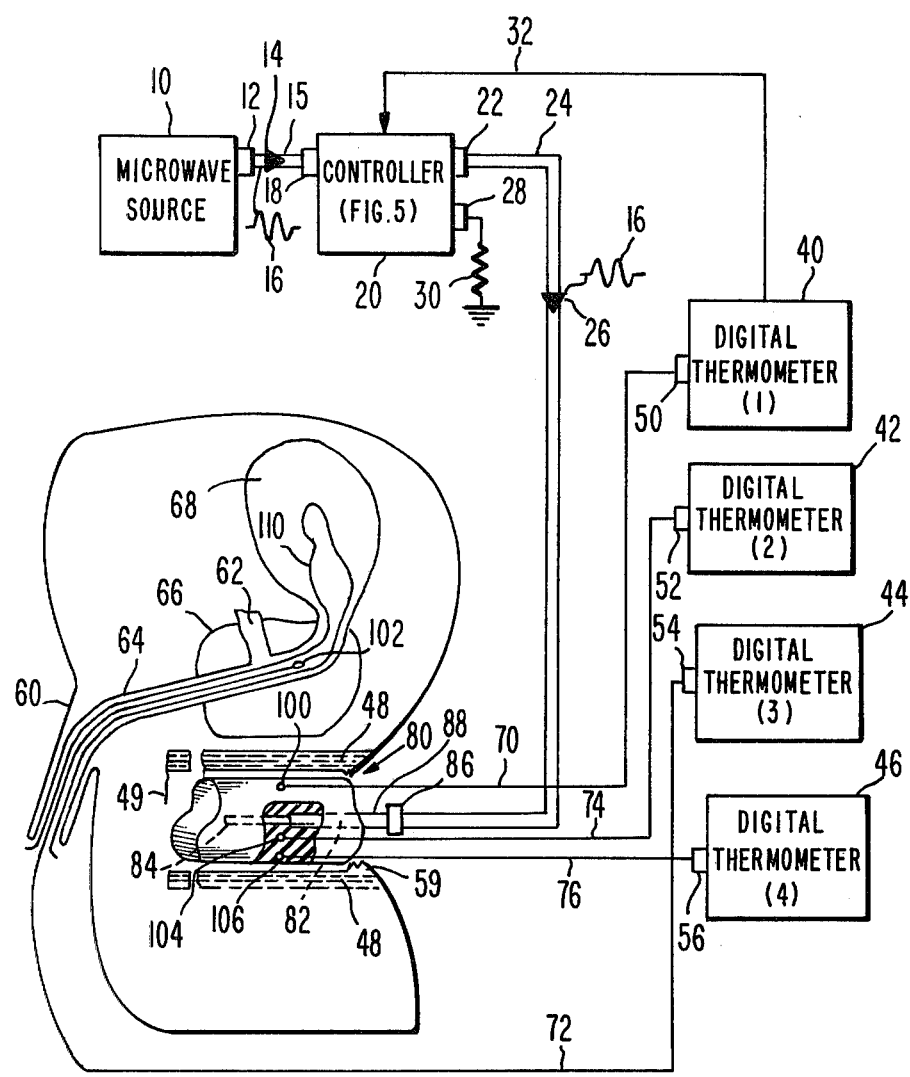
FIG. 1 is a block schematic of an apparatus of one embodiment of the invention.

The symbols and the relative positions, shown in FIG. 1, of the organs of the human male body, such as prostate gland 66, penis 60, urinary bladder 68, rectum 48, anus 59, urethra 64, and ejaculatory ducts 62 are for illustrative purposes only. For an authoritative source on the actual positions and descriptive information on each of the organs, consult for example, *Anatomy*, by Henry Gray, 1977, Bounty Books, N.Y.

The colon 49 is that part of the large intestine (not shown) extending from the cecum (not shown) to the rectum 48. The prostate gland 66 is the male organ situated at the base of the urinary bladder 68 and surrounds the upper portion of a duct called the urethra 64. The urethra 64 passes the urine from the urinary bladder 68 and the seminal fluids, via the ejaculatory ducts 62, out of the body. Medical practioners have known that the prostate gland may be accessed for examination via the anus 59 of the rectum 48. The examining physician positioning an instrument, such as his finger, may determine if the prostate gland 66 is or is not enlarged by palpating a portion of the prostate gland 66. The invention to be described uses the accessibility to the prostate gland 66 via the anus 59, the rectum 48 and the colon 49 for positioning an applicator 80 to launch microwave energy for preferential irradiation of the prostate gland 66. Applicator 80 radiates electromagnetic energy in response to a microwave signal 16 supplied from a microwave souce 10. The microwave signal 16 is transmitted in the direction of arrow 14, via a coaxial connector 12, a coaxial cable 15 and a coaxial connector 18, to a controller 20. Controller 20 transmits the microwave signal 16, in the direction of arrow 26, via a coaxial connector 22, a coaxial cable 24 and a coaxial connector 86, to applicator 80. The microwave signal 16 is launched from the junction of the unshielded end 84 and choke 82 of applicator 80 towards the prostate to generate heat for therapeutic and hyperthermic treatment of the prostate gland 66 as will be described in greater detail hereinbelow.

The means for measuring the heat within the environment heated by the microwave signal 16 is provided by temperature sensing elements, such as thermocouples 100, 104, and 106. If desired, a thermocouple 102 shown in FIG. 1, may be centrally positioned at the prostate gland 66 via the entrance into the urethra 64 through the penis 60. As will be explained hereinafter, the temperature of the prostate gland 66 elevated by irradiating signal 16 may be known within a reasonable accuracy without the use of thermocouple 102 from empirical data derived from experimental use of thermocouples 100, 104 and 106 positioned on applicator 80. However, the placement of the thermocouple 102 within the central portion of prostate gland 66 will be discussed. To place thermocouple 102 at the central portion of the prostate gland 66 a conventional catheter 110 is inserted into the urethra 64 via the penis 60 and thus positioned into the urinary bladder 68. The conventional catheter 110 may be of the type such as an ACMIX catheter, type 5CC, size 16FR, manufactured by American Latex Corporation subsidiary of A.C.M.I., Sullivan, Ind. The catheter 110 is inserted, using known procedures, via the urethra 64, into the urinary bladder 68. The balloon at the end of catheter 110 is then inflated with 5CC of air by use of a syringe used in conjunction with the Foley catheter 110. The catheter 110 is then withdrawn to be positioned at the neck of a urinary bladder 68, such that the inflated portion of the catheter 110 prevents further entrance into the urethra 64. Thermocouple 102 is then inserted into the catheter 110 to a position three centimeters from the inflated portion of the catheter 110. The three-centimeter distance places the thermocouple 102 at the central portion of the prostate gland 66 to measure the environmental temperature of the prostate gland 66 elevated by the microwave signal 16 launched from applicator 80.

Figure 2:
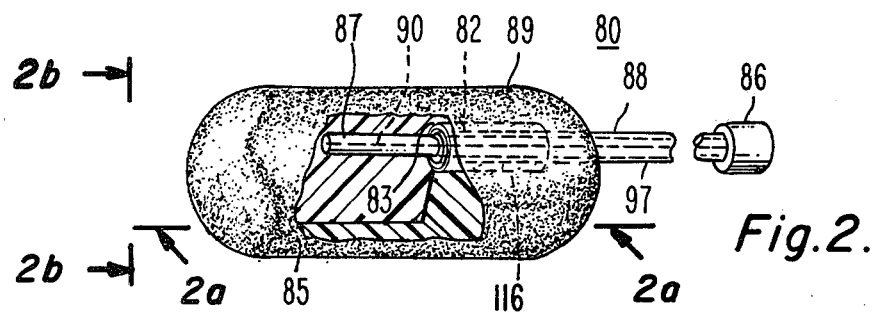
FIGS. 2, 2A and 2B are schematics of the applicator.
Figure 2A:
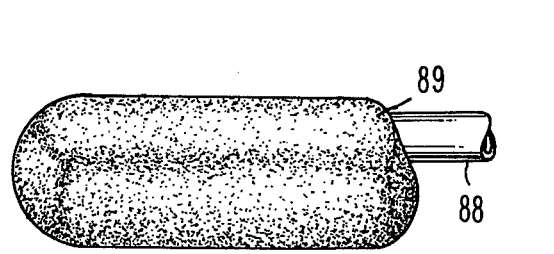
Figure 2B:
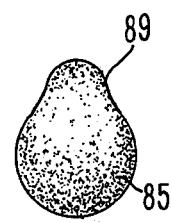
Figures 3, 7:
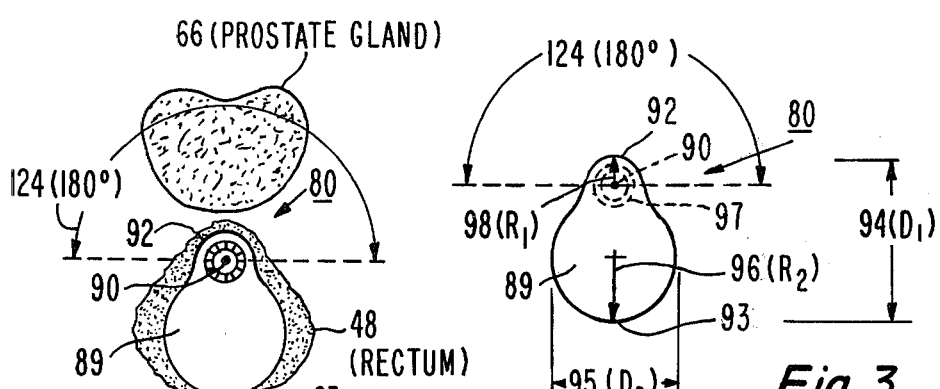
FIG. 3 is an end view of the applicator with certain dimensioned relationships.
FIG. 7 is a sectional view showing the positioning of the applicator within the rectum and in relation to the prostate gland.

FIGS. 2, 2A and 2B show several views partly in section of the irregularly shaped end of applicator 80 formed of a smooth dielectric material 85 such as teflon. The bulb end 89 of applicator 80 has an irregular shape as shown by side view 2A (FIG. 2A) and end view of 2B (FIG. 2B). Further details of the irregularly shaped end of 89 of applicator 80 are shown in FIG. 3; irregularly shaped bulb 89 having a top segment 92 of the narrow portion and a bottom segment 93 of the wide portion, radii 98 ($R_1$) and 96 ($R_2$) and diameters 94 ($D_1$) and 95 ($D_2$). Radius 98 ($R_1$) has a typical value equal to one-quarter inch (0.635 cm). Radius 96 ($R_2$) has a typical value equal to one-half inch (1.270 cm). Diameter 94 ($D_1$) has a typical value equal to one inch (2.54 cm). Diameter 95 ($D_2$) has a typical value equal to 0.9 inches (2.29 cm). The typical values for radii 96 and 98 and diameters 94 and 95 given hereinbefore are for a normal-sized man. It should be understood that these typical values may be altered in accordance with the dimensions of the rectum 48 and colon 49 for the body receiving the hyperthermia treatment. It should be further understood that decreasing the dimensions of the applicator, decreases possible irritation occurring when applicator 80 is positioned into a body cavity such as rectum 48 and colon 49.

Figure 4:
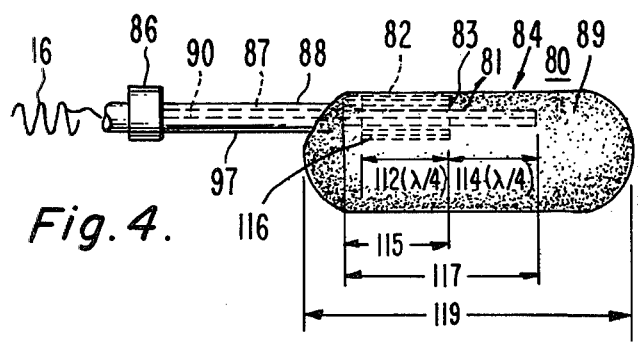
FIG. 4 is a side view of the applicator showing the choke and unshielded end combining to serve as the radiator.

Applicator 80, as best seen in FIG. 4, has a connector 86, and a coaxial cable 97 having an inner conductor 90 and an outer conductor 88. The outer conductor 88 has an outer diameter having a typical value of 0.25 inches (0.635 cm). The outer conductor 88 is formed of a semi-rigid conductive material such as copper. Connector 86 is a suitable microwave connector such as a Model 1511 Precision Connector manufactured by Weinschel Engineering Inc., Gaithersburg, Md. Coaxial cable 97 has a dielectric material 87 such as teflon, between the outer and inner conductors 88 and 90 respectively. Coaxial cable 97 is suitably a microwave cable such as a Model UT-250A, manufactured by Uniform Tube, Inc., Collegeville, Pa. A choke 82 and the unshielded end 84 are internally positioned within the bulb 89. The choke 82 and the outer conductor 88 are rigidly joined by a solder junction 83. The unshielded end 84 extends a distance 114 from the junction 83 towards the distal end of bulb 89. Choke 82 extends a distance 112 from the junction 83 towards the entrance position of the coaxial cable 97 into the bulb 89. The outer conductor 88 of coaxial cable 97 is insulated from the choke 82, except at junction 83, by a sleeve 116 of dielectric material such as teflon, to prevent choke 82 from contacting outer diameter 88 except at noninsulated junction 83. Unshielded end 84 having a distance 114 and choke 82 having a distance 112 form a half-wave dipole radiator 81 having junction 83 as its feed-point for launching microwave signal 16. Distances 112 and 114 are equal to $\lambda_g/4$ where $\lambda_g$ is defined by the following equation:

$$\lambda g = \frac{c}{f \sqrt{\epsilon}}$$

where c is the speed of light in vacuum and is equal to $3.0 \times 10^8$ meters/sec., f is the microwave frequency in cycles per second, and $\epsilon$ is the dielectric constant of the medium 87, such as teflon, between the inner conductor 90 and outer conductor 88. Using equation (1) for a typical value of f equal to 2.45 GHz distances 112 and 114 are equal to 0.831 inches (2.11 cm). Choke 82 is a suitable hollow metallic sleeve, having an inner diameter of 0.277 inches (0.704 cm) for positioning about the 0.25 inch (0.635 cm) outer diameter of outer conductor 88. Outer conductor 88 extends into the teflon bulb 89 a distance 115 equal to 1.31 inches (3.33 cm) for the typical microwave frequency of 2.45 GHz. The combined distance of the outer conductor 88 and the unshielded end 84 extending into bulb 89 is shown as a distance 117 and is equal to 2.15 inches (5.46 cm). The longitudinal length of teflon bulb 89 is shown as distance 119 and is equal to a value of 2.5 inches (6.35 cm). The characteristic impedance ($Z_0$) of the coaxial cable 97 of the applicator 80 can be represented by the following equation:

$$Z_0 = \frac{138}{\sqrt{\epsilon}} \log_{10} \frac{b}{a} \qquad (2)$$

where $\epsilon$ is the dielectric constant of the medium 87 between the inner 90 and outer 88 conductors and "a" and "b" are respectively the inner and outer conductor diameters. For a characteristic impedance of 50Ω, $1/\sqrt{\epsilon}$ is 0.69 for teflon, "a" equals 0.0625 inches (0.1587 cm) and "b" equals 0.210 inches (0.533 cm).

Figure 5:
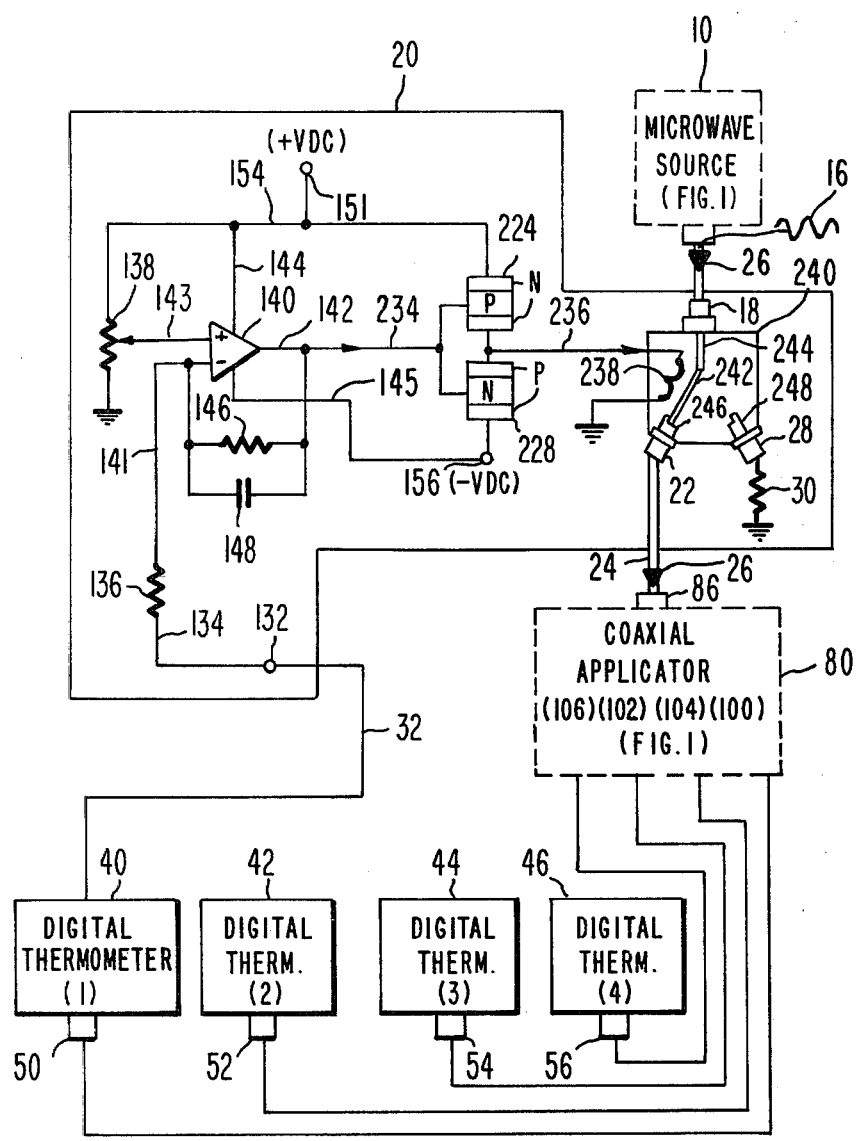
FIG. 5 is a schematic of the controller (20) of FIG. 1.

Reference is now made to FIG. 5 for the details of controller 20 shown in FIG. 1. Controller 20 has a coaxial switch 240 which connects microwave signal 16 either to connector 22 for further coupling to applicator 80 or to connector 28 for further coupling to a dummy load 30. Coaxial switch 240 is suitably a Hewlett-Packard switch, part number 8761A. Switch 240 includes an input coaxial connector 18, two output coaxial connectors 22 and 28, and a flexible reed contact 242 that is magnetically coupled to winding 238. Each of the coaxial cable connectors 18, 22 and 28 have inner conductors 244, 246 and 248 respectively. Reed contact 242 is connected at one end to the center conductor 244 of input connector 18 and the other end thereof is positionable in response to signals passing through the winding 238 to be electrically connected with either inner conductor 246 or 248. The polarity of the voltage applied to winding 238 determines the position to which reed contact 242 is connected. A positive voltage applied to winding 238 positions reed contact 242 to inner conductor 246 of coaxial connector 22 and thus connects microwave signal 16 to applicator 80 via connector 86 for further coupling to prostate gland 66. Conversely, a negative voltage applied to winding 238, positions the reed contact 242 to the inner conductor 248 and thus connects microwave signal 16 to the dummy load 30. Dummy load 30 provides a proper termination of the microwave signal 16 when signal 16 is not applied to coaxial applicator 80.

The application of a positive or negative energizing signal to winding 238 is controlled by differential amplifier 140 operating with transistors 224 and 228. Differential amplifier 140 is suitably a type RCA CA741. Transistor 224 is suitably an NPN type and transistor 228 is suitably a PNP type. Differential amplifier 140 has two inputs, one a non-inverting input on signal path 143 and the other an inverting input on signal path 141. The input on path 143 is preset to a d.c. value indicative of a predetermined temperature that is to be maintained for the tissue in contact with the thermocouple 100. The preset value is set by adjusting the potentiometer 138. The potentiometer 138 is connected between a voltage source having a positive polarity, such as a positive d.c. voltage connected at terminal 151, and a reference voltage, such as ground, such that the preset value of potentiometer 138 is adjustable therebetween. The input voltage to differential amplifier 140 on signal path 141 is suitable to d.c. voltage, proportional to temperature measured by a digital thermometer 40 which is connected to signal path 141 via a resistor 136, a signal path 134, a terminal 132 and a signal path 32. Digital thermometer 40 (and also digital thermometers 42, 44 and 46 to be discussed) is suitably a Model No. BAT -8 manufactured by the Bailey Instrument Co. of Saddle Brook, N.J. The voltage present on signal path 141 is indicative of a temperature of the tissue measured by thermocouple 100. Differential amplifier 140 is connected to a positive voltage supply at terminal 151 and a negative voltage supply at terminal 156 via busses 144 and 145 respectively. Differential amplifier 140 develops an output voltage on path 142 proportional to a differential voltage existing between the input signal paths 143 and 141. When the voltage level on signal path 141 is less than the voltage level of the preset value at input path 143, differential amplifier 140 produces a positive voltage on path 142. The positive voltage on path 142 is further conducted to transistor 224 via a signal path 234. The positive voltage on path 142 renders transistor 224 conductive. Transistor 224 being conductive generates a positive voltage, via path 236, to winding 238 of coaxial switch 240, thereby providing a path for connecting microwave signal 16 to applicator 80. When the voltage level on path 141 exceeds the voltage level on the preset value at input 143, a negative voltage is generated by differential amplifier 140 on path 142 turning off transistor 224 and making transistor 228 conductive. Transistor 228 being conductive, generates a negative voltage, via path 236, to winding 238 of coaxial switch 240 thereby removing microwave signal 16 from applicator 80 and further connecting microwave signal 16 to the dummy load 30. Resistor 146 and capacitor 148 connected between inverting input path 142 and output path 142 of amplifier 140 form a feedback network that determines the response time and gain of differential amplifier 140 with regard to the differential signals between paths 143 and 141.

In operation, when the temperature of the tissue site, as measured by thermocouple 100, is below the preset value as established by potentiometer 138, the microwave signal 16 is coupled via switch 240 to applicator 80. The signal 16 remains coupled to applicator 80 until the temperature as measured by thermocouple 100 equals or exceeds the preset value, whereby the microwave signal 16 is decoupled from applicator 80 and further coupled to dummy load 30. This action is repeated as switch 240 couples and decouples signal 16 from the applicator 80 in response to the change of temperature of the tissue as sensed by thermocouple 100.

Digital thermometers 42, 44 and 46 provide a visual means for monitoring the temperature of the tissue in contact with thermocouples 104, 102 and 106 respectively. If the temperatures measured by thermocouples 104, 102 and 106 exceed predetermined values, to be explained hereinafter, the microwave source 10 is manually turned off. If desired suitable logic, similar to differential amplifier 140, may be incorporated in controller 20 to provide automatic control for decoupling the microwave signal 16 from applicator 80 if any tissue temperature as measured by thermocouples 100, 102, 104 and 106 equals or exceeds predetermined values. However, as will be discussed hereinafter, it is only necessary to provide automatic control for decoupling microwave signal 16 from applicator 80 if the temperature of the tissue measured by thermocouple 100 equals or exceeds a predetermined value.

FIG. 7 is a cross-sectional view of the position of the applicator 80 within the rectum 48 with respect to the prostate gland 66. Teflon bulb 89 is inserted through the anus 59 (FIG. 1) into the rectum 48 and positioned opposite the tumorous prostate under treatment. FIG. 7 illustrates a prostate gland tumor under treatment, but it should be recognized that other tumors adjacent to the rectum 48 or colon 49 may be treated. Teflon bulb 89 is positioned with its top segment 92 abutting the walls of the rectum adjacent to the location of the prostate gland 66 and its bottom segment 93 abutting the walls of the rectum diametrically opposite the prostate gland 66. As will be explained, the microwave energy is radiated in a preselected direction to develop preferential heating of the prostate gland 66 relative to the heating of the tissue of the rectum 48 diametrically opposite prostate gland 66.

In hyperthermia treatment of cancer, such as cancer of the prostate, the cancerous lesion is preferably heated to the hyperthermia range, that is, approximately 42.0°–43.5° C. and typically maintained in this range for a period of one-half to one hour. Further, it is desirable that during the treatment of the cancerous lesion the healthy tissue be kept at a temperature close to the body temperature.

The irregular shape of teflon bulb 89 having the radius 98 ($R_1$), previously discussed with relation to FIG. 3, and a circular sector 124 equal to 180° having as its mid-point center conductor 90, develops a radiation pattern inside the rectum 48 that is concentrated within sector 124 equal to 180°. When the teflon bulb 89 is inserted into the rectum 48 most of the RF energy is directed toward the prostate gland 66. The reason for this directive radiation pattern is as follows:

(1) because of the pear-shaped geometry of the teflon bulb 89 the tissues of the rectum 48 within sector 124 are closest to the dipole antenna, and (2) since the dielectric constant of tissues e.g., 50 is many times as high as the dielectric constant of teflon i.e., 2.1 and also since RF electric fields tend to concentrate in the regions of highest dielectric constant, the RF radiation pattern is tilted toward the tissues in contact with sector 124. The microwave signal 16 launched from radiator 81 within sector 124 travels the minimum distance, that is, radius 98 ($R_1$), for penetration of the rectum 48. The microwave signal 16 launched from radiator 81 outside sector 124 will travel a farther distance than radius 98 ($R_1$). The power density of the launched signal 16 decreases approximately by the square of the distance traveled from the radiating probe, that is, the radiator 81. Thus, the maximum power density of signal 16 penetrating rectum 48 is within the sector 124 located at the top segment 92 of teflon bulb 89. Conversely, the minimum power density of signal 16 penetrating rectum 48 that travels a maximum distance from radiating probe 81 is at the bottom segment 93 of teflon bulb 89. The effect of the irregular shape of teflon bulb 89 is to transmit maximum energy in the 180° direction to the rectum 48 located adjacent to prostate gland 66. The maximum intensity of microwave signal 16 penetrates the wall of the rectum 48 and is further transmitted towards, penetrates and heats the prostate gland 66. Conversely, the irregular shape of teflon bulb 89 provides for a less intense signal 16 to penetrate and thus heat the remainder of the wall of rectum 48 in a relatively less intense manner. The heat developed by the microwave signal 16 is directly proportional to the intensity of the transmitted signal 16. The maximum heat is developed at the wall of the rectum 48 within the sector 124 of applicator 80 which is adjacent to the prostate gland 66 and thus provides preferential heating of the prostate gland 66. The wall portions of rectum 48 in contact with applicator 80 outside the sector 124 are heated non-uniformly in accordance with the square of the distance traveled by microwave signal 16 from the radiator 81. Thus, the farther the distance traveled by microwave signal 16 the less intense is the heat developed at such rectum (48) wall portions.

It should be recognized that the teflon bulb 89 may be designed to provide predetermined sector angles 124 other than 180°. The location of the inner conductor 90 within the teflon bulb 89 is the origin of the radius 98 ($R_1$). Radius 98 ($R_1$) defines the minimum distance traveled by the microwave signal 16 before it exits the teflon bulb 89 to irradiate the tissue. The shape of the teflon bulb 89 and the position of the inner conductor 90 may be designed, for example, to provide a top segment 92 whereby the arc of the radius 98 ($R_1$) forms a 90° sector.

Referring to FIGS. 6a and 6b there is shown experimental heating patterns developed by applicator 80 implanted in ground beef (not shown). The temperature increases at the nine locations (1 to 9) shown in FIG. 6a were developed by heating the ground beef with a microwave signal 16, having an intensity of 3.0 watts and a frequency of 2.45 GHz, for 7 minutes. FIG. 6a shows a radial distribution of temperature increases about applicator 80, having a radius 96 ($R_2$) of 0.375 inches (0.95 cm), in a plane perpendicular to the major axis of the applicator 80 at junction 83. The microwave signal 16 launched from dipole antenna 81 (shown in FIG. 6b) develops the relatively highest temperature increases or hottest temperature near the top segment 92. Conversely, the microwave signal launched from dipole antenna 81 develops the relatively lowest temperature increases or coldest temperature near the bottom segment 93.

FIG. 6b shows the temperature increases of 36 locations, referenced to the innermost position 91 of the top segment 92 (FIG. 6c). The temperature increases were developed by heating the ground beef with microwave signal 16 having an intensity of 3.0 watts and a frequency of 2.45 GHz, launched from dipole antenna 81 for four minutes. The Y axis of FIG. 6b is distance l, in cm, in the vertical direction from point 91. The X axis at distance w, in cm, in a horizontal direction from point 91. The temperature increases of the 36 locations have the values shown in FIG. 6b and these values are in °C. The maximum temperature increase, shown along the X axis as 5.1° C., occurs at point 99 which is located along the top segment 92. Point 99 is approximately 2.5 cm from point 91.

It should now be appreciated that the temperature distribution, shown in FIG. 6a, about the teflon bulb 89 develops a preferential heating of the ground beef, within a preselected direction established by sector 124, relative to the heating of the ground beef outside the sector 124. Also the highest temperature along the top segment 92, shown in FIG. 6b, occurs at the position 99. As will be described hereinafter, in reference to FIG. 8, the preferential heating provided by sector 124 and the known location 99 where the hottest temperature along the top segment 92 will occur is used to position the teflon bulb 89 in the rectum 48 to elevate the temperature of the prostate gland to the hyperthermic range.

While the preferred embodiment provides means to measure the temperature at the interface of the applicator and the tissue being treated, it should be understood that the temperature does not have to be controlled during the treatment. Thus, for example, past performance data can be used to operate the applicator for a time period at a power level predetermined from such data to effectively generate the heat required without direct temperature control.

Reference is now made to FIG. 1 to describe the placement of thermocouples 100, 104 and 106 on applicator 80. Thermocouples 100, 104 and 106 are positioned about and in line with junction 83 and suitably affixed to the periphery of teflon bulb 89 prior to the insertion of the teflon bulb through the anus 59 into the rectum 48. Thermocouple 100, connected to digital thermometer 40 via path 70 and connector 50, is positioned and affixed to the top segment 92 of teflon bulb 89 that is to be positioned at the wall of the rectum 48 adjacent the prostate gland 66. Thermocouple 104, connected to digital thermometer 42 via path 74 and connector 52, is positioned and affixed to the periphery of teflon bulb 89 typically 120° from thermocouple 100. Thermocouple 106, connected to digital thermometer 46 via path 76 and connector 56, is positioned and affixed to the bottom segment 92 of teflon bulb 89 which is to be located at the wall of the rectum 48 that is diametrically opposite from the wall of rectum 48 adjacent the prostate gland 66. After the thermocouples 100, 104 and 106 are affixed to applicator 80 a suitable expandable rubber material, such as a latex finger cot, is placed over the periphery of applicator 80 which is to be inserted through the anus 59 into the rectum 48 to thus prevent the substances of the human body from directly contacting applicator 80 and further to prevent any irritation by thermocouples 100, 104 and 106 to the rectal and colon linings when the teflon bulb 89 is inserted through the anus 59 into the rectum 48 or colon 49.

The applicator 80 is inserted, via the anus 59, into the human rectum 48. The rectum 48 is the lower terminal 8 (20.3 cm) to 10 inches (25.4 cm) of the large intestine. The anus 59, as previously noted, is the termination of the rectum 48, while the colon 49 is that part of the large intestine extending from the cecum to the rectum 48. The applicator 80 is positioned within the rectum 48 such that the top segment 92 of the teflon bulb 89 is located at the wall of the rectum 48 in close proximity with respect to the prostate gland 66. The alignment of the top segment 92 of the teflon bulb 89 to the prostate gland 66 and the previously discussed positioning of the thermocouple 102 in the urethra 64 may be verified by an imaging scanning device which may scan the lower part of the torso. Upon verification of the correct positioning of the applicator 80 within rectum 48 and thermocouple 102 within the uretha 64, the irradiating microwave signal 16 is connected to applicator 80 via coaxial cable 24 and the connector 86.

Microwave source 10 is selected to provide a predetermined frequency for microwave signal 16. A microwave frequency of 915 MHz for signal 16 provides a penetration depth of 3 cm for the type of tissue being treated such as the prostate gland 66. Similarly, a microwave frequency of 2.45 GHz for signal 16 provides a penetration depth of 1.7 cm. Microwave signal 16 typically has an intensity of 2.5 watts for the hyperthermia treatment of a prostate gland 66 having a typical diameter of 2.5 cm.

As previously discussed, the maximum intensity of the microwave signal 16 launched from the radiator 81 of applicator 80 is within the sector 124 at the top segment 92 of teflon bulb 89. Microwave signal 16 penetrates the walls of the rectum 48 and the prostate gland 66 to irradiate and thus heat and elevate the temperature of the prostate gland 66 and the walls of the rectum 48 adjacent the prostate gland 66.

Thermocouple 100 measures the temperature at the top segment 92 of the teflon bulb 89 in contact with the walls of the rectum 48 adjacent the prostate gland 66. Thermocouple 104 measures the temperature of the tissue in contact with the central outer portion of the teflon bulb 89. Thermocouple 106 measures the temperature of the walls of the rectum 48 in contact with the bottom segment 93 of teflon bulb 89 which is positioned diametrically opposite the walls of the rectum 48 adjacent to the prostate gland 66. The rubber material placed over the periphery of applicator 80 and thus positioned between the tissue and thermocouple 100, 104 and 106, affects the speed of response for thermocouples 100, 104 and 106 to measure the temperature of the tissue. However, the rubber material, when heated, conducts heat and thermocouples 100, 104 and 106 will measure the temperature of the tissue of which they are in contact. Thermocouple 102, connected to digital thermometer 44 via path 72 and connector 54, measures the temperature within the general environment of the prostate gland 66. A representative temperature measured by thermocouple 100 is approximately 4° C. higher than the temperature measured by thermocouple 102. The temperature measured by thermocouple 102 is approximately 2° C. higher than the tissue measured by thermocouple 104. Finally, thermocouple 104 measures a temperature of approximately 2.5° C. higher than thermocouple 106.

As previously discussed, controller 20 operates to decouple the microwave 16 from applicator 80 and thus prevents further irradiation of the treated tissue if the temperature of the tissue in contact with thermocouple 100 equals or exceeds a preset value. Potentiometer 138 of controller 20, operating with thermocouple 100 is typically adjusted to establish a preset value of approximately 43° C. The temperature of the tissue in contact with thermocouple 100 is the maximum temperature to which the tissue, treated by microwave signal 16, is to be elevated and thus the critical temperature that is automatically controlled. The temperature of the tissue in contact with thermocouples 104, 102 and 106 is displayed by digital thermometers 42, 44 and 46, respectively, and if these temperatures exceed a predetermined value, typically 43° C., the microwave source 10 is manually turned-off thereby preventing damage to the tissue. If none of the preset values are exceeded, microwave signal 16 irradiates the treated tissue, in particular, the prostate gland 66, to heat and maintain the prostate gland 66 to the hyperthermia range. It should be noted that the described embodiment of the invention is not limited to the hyperthermia treatment of a cancerous prostate gland 66. The microwave signal 16 may also be used for hyperthermia treatment of an enlarged, but not malignant, prostate gland 66. This application of microwave signals is similar in effect to the well-known sitz bath treatment. Microwave signal 16 elevates the temperature of the prostate gland 66 such as to cause an enlarged prostate gland 66 to decrease in size and return to a normal size. A normal size prostate gland manifests a normal urine flow rate as the urinary bladder 68 is drained via the urethra 64.

Figure 8:
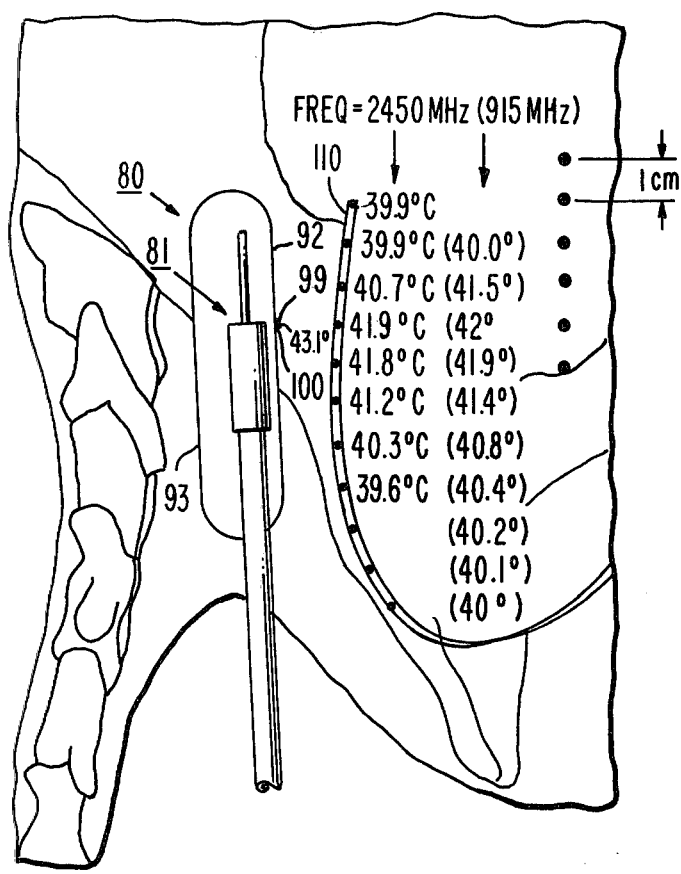
FIG. 8 shows an operative example of the use of the applicator in an experiment conducted on a male dog.

Reference is now made to FIG. 8 to discuss the results of an experiment conducted at Montefiore Hospital in Bronx, New York, using an anesthetized male dog. Heating was developed in the anesthetized male dog when the dog was heated with applicator 80 having dimensions for microwave frequencies of 915 and 2450 MHz. FIG. 8 shows a sketch made from an x-ray taken of the male dog with an internally positioned applicator 80 having the dimensions according to a 2.45 GHz operating frequency. Thermocouple 100 was positioned on the periphery of teflon bulb 89 at the previously described location 99. Top segment 92 of teflon bulb 89 was positioned at the walls of rectum 48 adjacent to the prostate gland 66. A thermocouple was internally positioned in a cathether 110 that was inserted into the urethra of the male dog. The temperatures shown along catheter 110 were measured in the urethra while the hottest spot, that is location 99 on the wall of the rectum, was measured by thermocouple 100 and maintained at 43.1° C. The temperature measurements shown for the heating developed by a 915 MHz microwave signal were made with a teflon bulb 89 having the same diameter as the 2.45 GHz applicator but having a length suitable for a 915 MHz dipole antenna, i.e. 5.35 inches (13.6 cm). The hottest temperature in the urethra developed by the 2.45 GHz applicator was 41.9° C. and was located 1 to 2 cm from top segment 92. Similarly, the hottest temperature in the urethra developed by the 915 MHz applicator was 42° C. and was located 1 to 2 cm from the top segment 92. The temperature difference between the hottest part 43.1° C. of the lining of the rectum and the hottest part of the urethra of the male dog was approximately 1.2° C. for the 2.45 GHz applicator and 1.1° C. for the 915 MHz applicator. Thus the 2.45 GHz and 915 MHz frequencies can develop preferential heating to elevate the temperature of tumors located 1 to 2 cm from the walls of the rectum. Also the highest temperature of the wall of the rectum was 43.1° C. thus preventing damage to the healthy body tissues located at the lining of the rectum.

It should be understood that the practice of this invention is not limited to hyperthermia treatment of the prostate gland 66. The invention may be practiced for the treatment of surface tissue (skin, etc.) and internal body tissue. The applicator 80 may be positioned at the body surface e.g., the axilla for treatment of surface tissue under the arm. Conversely, the applicator 80, suitably dimensioned, may be entered into the body through the mouth and positioned in a passageway such as the throat for treatment of the lungs. It should be further understood that the practice of this invention is not limited to the male body. For example, applicator 80, may be arranged to enter into a female body through a passageway such as the vagina for treatment of the uterus by the use of microwave signals. It should still further be understood that the invention is not limited to the human body since it may be practiced on animals.

What is claimed is:

1. Apparatus for the hyperthermic treatment of selected living tissue internal to a body with microwave energy comprising:
   a. source means for providing microwave signals having a predetermined amplitude and frequency; and
   b. means for preferentially heating said selected tissue by applying said microwave signals to said selected tissue and living tissue adjacent to said selected tissue;
   said preferential heating means for use within a passageway of said body and including a radiating probe coupled to said source means of microwave signals and a nonsymmetrical dielectric bulb, said bulb being configured and affixed to said probe to provide an electric field of said microwave signals from said probe that is more intense towards said selected tissue than towards said adjacent tissue when said bulb is properly positioned within said passageway of said body relative to said selected tissue.

2. Apparatus according to claim 1 further comprising temperature sensing means positioned on the periphery of said preferential heating means at the wall of said passageway in close proximity to said selected body tissue to provide an electrical signal indicative of the temperature of the wall of said passageway in close proximity to said selected body tissue.

3. Apparatus according to claim 2 further comprising control means responsive to said electrical signal for coupling said microwave signals to said preferential heating means when the temperature of said selected tissue is less than a predetermined temperature.

4. Apparatus according to claim 3, wherein said control means comprises:
   a. means for generating an electrical signal indicative of a predetermined reference temperature;
   b. means responsive to said signal indicative of said predetermined temperature and said signal indicative of the temperature of the wall of said passageway in close proximity to said selected body tissue for generating an output signal when said predetermined temperature exceeds the temperature of the wall of said passageway in close proximity to said selected body tissue.

5. Apparatus according to claim 1 wherein said bulb has first and second cross-sectional segments, with said first segment being relatively thin compared to said second segment, and wherein said radiating probe is situated entirely within said bulb with its axis parallel to the axial extension of said bulb and perpendicular to said cross-sectional segments, said radiating probe positioned at approximately the juncture of said segments to provide preferential heating in the direction of said relatively thin segment.

6. Apparatus according to claim 5, wherein said radiating probe has a length equal to an integral multiple of one-half wavelength of the wavelength of said microwave signal.

7. Apparatus according to claim 6, wherein said radiating probe comprises an unshielded coaxial cable and a hollow cylindrical means surrounding the outer diameter of said coaxial cable, said unshielded coaxial cable and said hollow cylindrical means each having a length equal to one-quarter wavelength of the wavelength of said microwave signal, said cylindrical means being connected to said outer diameter at one end of said unshielded cable.

* * * * *